US007699915B2

(12) United States Patent
Lin

(10) Patent No.: US 7,699,915 B2
(45) Date of Patent: Apr. 20, 2010

(54) LIQUID IMPINGEMENT UNIT

(75) Inventor: Chun-Wah (Phil) Lin, Hayward, CA (US)

(73) Assignee: Microfluidic Systems, Inc., Fremont, CA (US)

( * ) Notice: Subject to any disclaimer, the term of this patent is extended or adjusted under 35 U.S.C. 154(b) by 815 days.

(21) Appl. No.: 11/509,879

(22) Filed: Aug. 24, 2006

(65) Prior Publication Data

US 2008/0047438 A1 Feb. 28, 2008

(51) Int. Cl.
*B01D 47/02* (2006.01)

(52) U.S. Cl. .............................. 96/413; 96/329; 95/82; 210/656; 73/23.22; 73/31.05; 73/31.07; 73/863

(58) Field of Classification Search .................. 96/329, 96/413; 210/656; 95/82; 73/23.22, 31.05, 73/31.07, 863
See application file for complete search history.

(56) References Cited

U.S. PATENT DOCUMENTS

| | | | | | |
|---|---|---|---|---|---|
| 3,522,734 | A | * | 8/1970 | Curby | 73/863.21 |
| 3,668,825 | A | * | 6/1972 | McIlvaine | 95/8 |
| 4,224,828 | A | * | 9/1980 | Steinke | 73/863.21 |
| 5,119,684 | A | * | 6/1992 | Pike | 73/863.22 |
| 5,154,891 | A | * | 10/1992 | Brenner | 422/102 |
| 5,385,026 | A | * | 1/1995 | Zhang et al. | 62/50.7 |
| 6,520,034 | B1 | * | 2/2003 | Masquelier et al. | 73/863.21 |
| 6,550,347 | B2 | * | 4/2003 | Bradley | 73/863.21 |
| 2005/0006310 | A1 | * | 1/2005 | Agrawal et al. | 210/640 |
| 2005/0016715 | A1 | * | 1/2005 | Werner et al. | 165/104.33 |
| 2006/0186048 | A1 | * | 8/2006 | Tan | 210/656 |

* cited by examiner

*Primary Examiner*—Robert J Hill, Jr.
*Assistant Examiner*—Christopher P Jones
(74) *Attorney, Agent, or Firm*—Haverstock & Owens LLP

(57) ABSTRACT

A modified liquid impingement unit is configured to automatically maintain a volume of buffer solution within a determined range, the buffer solution used to collect airborne particles from an impinging airflow. The liquid impingement unit includes a first end of an air nozzle and a first end of a vacuum tube sealed within collection vessel. A fluid delivery tube is positioned within the vacuum tube such that a first end of the fluid delivery tube is also positioned within the sealed collection vessel. External to the sealed collection vessel, the fluid delivery tube branches from the vacuum tube through an aperture in the vacuum tube. The vacuum tube is coupled to a vacuum pump and the fluid delivery tube is coupled to a fluid pump. A control module provides control signals to the fluid pump such that the fluid pump delivers a second volume of buffer solution from a buffer solution container to the collection vessel via the fluid delivery tube.

20 Claims, 3 Drawing Sheets

LIQUID IMPINGEMENT UNIT

GOVERNMENT LICENSE RIGHTS

This invention was made with Government support under Agreement No. W81XWH-04-9-0010 awarded by the Government. The Government has certain rights in this invention.

FIELD OF THE INVENTION

The invention relates to a liquid impingement unit. More particularly, the invention relates to a liquid impingement unit included within an air collection device and used to collect airborne particles in a liquid.

BACKGROUND OF THE INVENTION

Bio-threat detectors are used to monitor the ambient air to detect the presence of potentially harmful pathogens. In general, air is drawn into an air collection and detection system where the particulates in the air are evaluated. Airflow into the system is typically generated by a fan or blower within the apparatus. One method of evaluating the airborne particles is to continuously monitor the air and the individual molecules within a given airflow. Some detection methods include the use of lasers to scan the air path in order to interrogate the particles passing through. A harmless particle, such as a dust particle, can be discriminated from a harmful particle, for example an anthrax spore, because each different type of particle reflects a different wavelength of light. The laser light reflected of the passing particles is matched to database of known harmful wavelengths. When a harmful wavelength is detected, the trigger signals that a potential pathogen is present.

Another method of evaluating the airborne particles within the airflow entering the system is to collect the airborne particles within a fluid sample and then analyze the fluid sample. One such device for collecting airborne particles in a fluid sample is a liquid impingement unit.

FIG. 1 illustrates a conventional liquid impingement unit. The liquid impingement unit 10 includes a collection vessel 12, an air nozzle 14, and a vacuum tube 16. The collection vessel 12 is hermetically sealed by a lid 18. The lid 18 is configured such that a first end of the vacuum tube 16 and a first end of the air nozzle 14 are sealed within the collection vessel 12. Air is forced out of the first end of the air nozzle 14 and into the collection vessel 12. The first end of the air nozzle 14 is positioned above a buffer solution 20 such that air output from the air nozzle 14 impinges the collection buffer solution 20. In this manner, airborne particles within the air are forced into the buffer solution 20. To prevent excess pressurization within the sealed collection vessel 12, the vacuum tube 16 removes air from within the collection vessel 12.

One disadvantage of conventional liquid impingement units is that the high air flow rate necessary to successfully implant the airborne particles within the buffer solution causes an increase in the evaporation rate of the buffer solution within the collection vessel. The evaporation rate is influenced by many factors, including, but not limited to, the surface area of the buffer solution-to-air interface within the collection vessel and the airflow rate out of the air nozzle. The vaporized liquid particles are removed from the collection vessel via the vacuum tube. A given fluid sample including the collected particles is generated over a given period of time, for example anywhere from about 10 minutes to 5 hours of continuous operation by the liquid impingement unit. The liquid impingement unit will lose a portion of the buffer solution due to evaporation and removal of the evaporated particles when the air is vacuumed from the collection vessel. For example, initially 10 ml of buffer solution is added to the liquid impingement unit, but after 5 hours of operation the volume of buffer solution remaining may be only 1 ml.

Over a period of time, the volume of the buffer solution within the collection vessel drops below a minimum operation level, at which point, the air collection process must be stopped either to removing the remaining buffer solution, including the collected particles within, or to add additional buffer solution to the collection vessel so that the total volume of buffer solution is above the minimum operation level. Either solution requires disruption of the air collection process, the manual removal of the hermetic lid from the collection vessel, and either the manual removal of the remaining buffer solution or the manual addition of more buffer solution to the collection vessel.

Due to evaporation of the buffer solution, operation of conventional liquid impingement units are limited in the amount of collection time that can be achieved for a given initial volume of buffer solution. Either the collection time is limited, which constrains the protocols of any system utilizing the liquid impingement unit, or additional buffer solution needs to be manually added into the collection vessel.

SUMMARY OF THE INVENTION

A modified liquid impingement unit is configured to automatically maintain a volume of buffer solution within a determined range, the buffer solution used to collect airborne particles from an impinging airflow. The liquid impingement unit includes a first end of an air nozzle and a first end of a vacuum tube sealed within collection vessel. A fluid delivery tube is positioned within the vacuum tube such that a first end of the fluid delivery tube is also positioned within the sealed collection vessel. External to the sealed collection vessel, the fluid delivery tube branches from the vacuum tube through an aperture in the vacuum tube. The vacuum tube is coupled to a vacuum pump and the fluid delivery tube is coupled to a fluid pump. A control module provides control signals to the fluid pump such that the fluid pump delivers a second volume of buffer solution from a buffer solution container to the collection vessel via the fluid delivery tube. In this manner, the volume of buffer solution in the collection vessel is automatically maintained according to control signals provided by the control module.

BRIEF DESCRIPTION OF THE DRAWINGS

Embodiments of the liquid impingement unit are described relative to the several views of the drawings. Where appropriate and only where identical elements are disclosed and shown in more than one drawing, the same reference numeral will be used to represent such identical elements.

DETAILED DESCRIPTION OF THE PRESENT INVENTION

Figure 1:
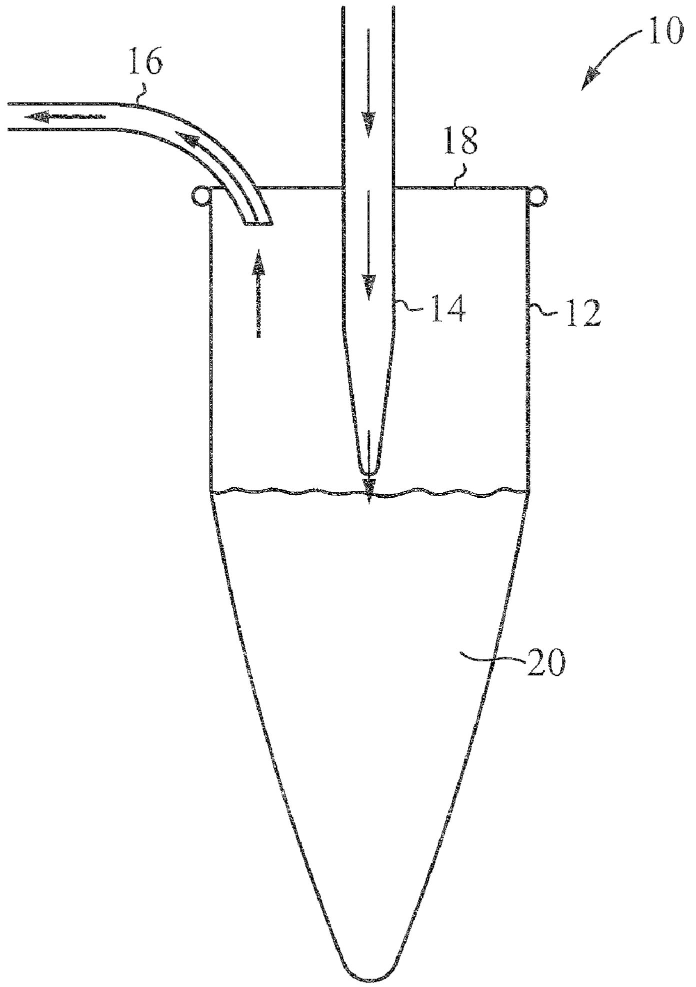
FIG. 1 illustrates a conventional liquid impingement unit.

Embodiments of the present invention are directed to a modified liquid impingement unit configured to automatically refill the collection vessel with buffer solution on a periodic basis. In this manner, the volume of the buffer solution is automatically maintained within a desired range over the course of operation of the liquid impingement unit. This desired range can be maintained over an indefinite period of time. The liquid impingement unit includes a collection vessel, an air nozzle, and a vacuum tube. A first volume of buffer solution is added to the collection vessel. A first end of the air nozzle and a first end of the vacuum tube are sealed within the collection vessel. A fluid delivery tube is positioned within the vacuum tube such that a first end of the fluid delivery tube is also positioned within the sealed collection vessel. In some embodiments, the first end of the fluid delivery tube extends into the buffer solution within the collection vessel.

External to the sealed collection vessel, the vacuum tube includes an aperture through which the fluid delivery tube exits. A second end of the vacuum tube is coupled to a vacuum pump. A second end of the fluid delivery tube, which is external to the vacuum tube, is coupled to a fluid pump. The fluid pump is configured to deliver a second volume of buffer solution from a buffer solution container to the collection vessel via the fluid delivery tube. A control module provides control signals to the fluid pump such that the fluid pump delivers the second volume of buffer solution. In this manner, additional buffer solution is automatically provided to the collection vessel according to control signals provided by the control module. In some embodiments, the control module is configured to instruct the fluid pump to deliver the second volume on a periodic basis. This period is determined based on a known evaporation rate of the first volume of buffer solution within the sealed collection vessel. Alternatively, one or more sensors are mounted within the collection vessel to monitor the first volume of the buffer solution within the collection vessel. Once the first volume decreases below a predetermined threshold, the control module instructs the fluid pump to deliver the second volume of buffer solution to the collection vessel. Still alternatively, the fluid pump delivers a continuous stream of buffer solution to the collection vessel. The continuous stream is provided at a determined rate based on the known evaporation rate.

A general function of the liquid impingement unit is to receive airflow including airborne particles, direct the airflow to the buffer solution within the collection vessel where the airborne particles are collected in the buffer solution, then periodically remove the buffer solution including the collected particles for processing. The particle collection efficiency of the liquid impingement unit decreases as the volume of buffer solution decreases. Therefore, in order to maintain efficiency of the liquid impingement unit, the volume of the buffer solution is maintained within an acceptable range.

Figure 2:
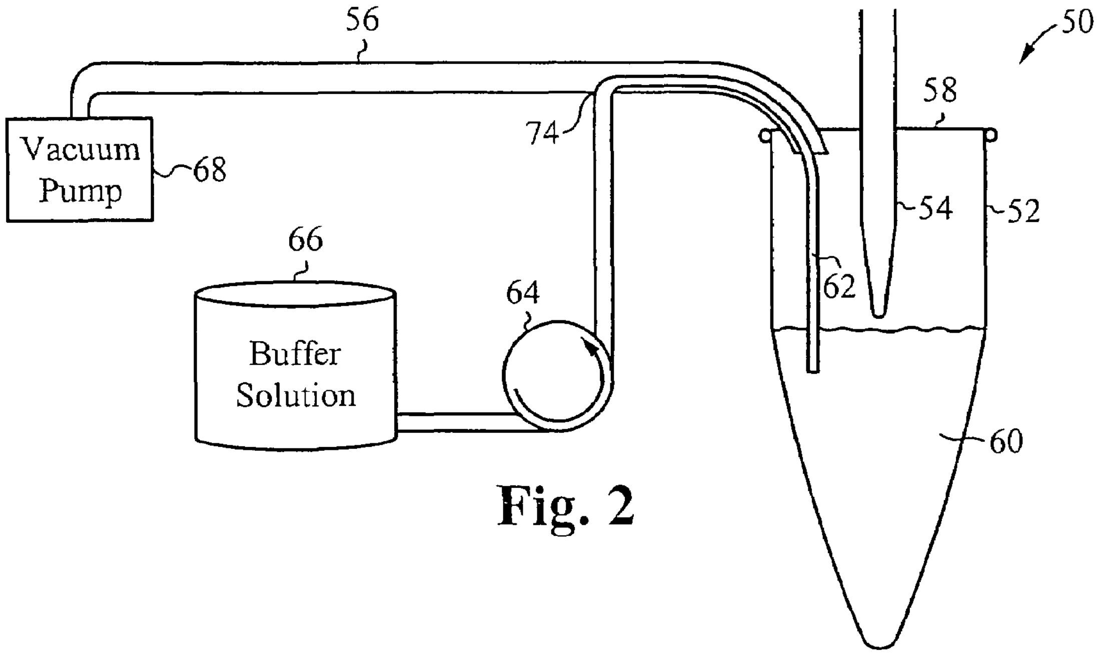
FIG. 2 illustrates a cut-out side view of an exemplary block diagram of one embodiment of a liquid impingement system of the present invention.

FIG. 2 illustrates a cut-out side view of an exemplary block diagram of one embodiment of the liquid impingement system of the present invention. The liquid impingement system 50 includes a collection vessel 52, an air nozzle 54, a vacuum tube 56, a fluid delivery tube 62, a fluid pump 64, a buffer solution container 66, and a vacuum pump 68. The collection vessel 52 holds a buffer solution 60.

The first end of the air nozzle 54 is positioned above and proximate to the surface of the buffer solution 60. The exact distance between the first end of the air nozzle 54 and the buffer solution surface is variable based on the volume of the buffer solution 60. The position of the first end of the air nozzle 54 relative to an initial volume of the buffer solution 60 is determined according to the airflow rate out of the air nozzle 54 and/or the dimensions of the collection vessel 52. The distance can also be experimentally determined based on a desired particle collection efficiency. As the volume of the buffer solution 60 decreases due to evaporation, the relative distance between the surface of the buffer solution 60 and the first end of the air nozzle 54 varies. In an alternative embodiment, the first end of the air nozzle is in contact with the surface of the buffer solution or is submerged beneath the surface of the buffer solution. In the alternative embodiment where the first end of the air nozzle 54 is initially submerged within the buffer solution 60, the surface of the buffer solution 60 may fall below the first end of the air nozzle 54 over the course of operation such that the first end is no longer submerged within the buffer solution 60.

A lid 58 seals the collection vessel 52 such that the first end of the vacuum tube 56 and the first end of the air nozzle 54 are hermetically sealed within the collection vessel 52. In some embodiments, an o-ring is positioned between the vacuum tube 56 and the lid 58 and an o-ring is positioned between the air nozzle 54 and the lid 58 to seal the unit. The fluid delivery tube 62 and the vacuum tube 56 are configured such that the fluid delivery tube 62 enters the vacuum tube 56 through an aperture 74 within the vacuum tube 56, and runs the remaining length of the vacuum tube 56 into the collection vessel 52, thereby circumventing the lid 58. The fluid delivery tube 62 exits the first end of the vacuum tube 56 and extends into the buffer solution 60. In some embodiments, the first end of the fluid delivery tube 62 extends beyond the first end of the vacuum tube 56, but not into the buffer solution 60. In some embodiments, the first end of the fluid delivery tube 62 coterminates with the first end of the vacuum tube 56.

A second end of the fluid delivery tube 62 is coupled to the fluid pump 64. The fluid pump 64 is coupled to the buffer solution container 66. In operation, the fluid pump 64 pumps buffer solution from the buffer solution container 66 through the fluid delivery tube 62 and into the collection vessel 52. In some embodiments, the fluid pump 64 pumps a set volume of buffer solution on a periodic basis. Alternatively, the fluid pump 64 continuously pumps buffer solution at a set rate.

Figure 3:
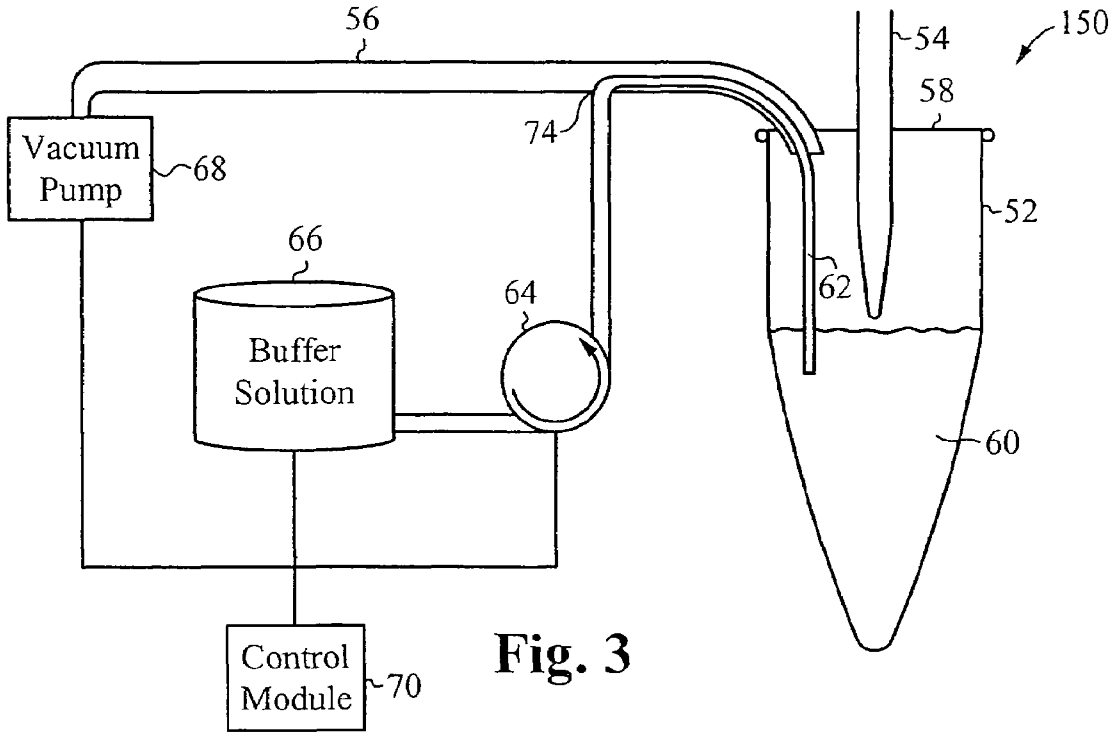
FIG. 3 illustrates one embodiment of an automated version of the liquid impingement system of FIG. 2.

FIG. 3 illustrates one embodiment of an automated version of the liquid impingement system of FIG. 2. The liquid impingement system 150 includes the liquid impingement system 50 of FIG. 2 and a control module 70. The control module 70 is coupled to the fluid pump 64, the buffer solutions container 66, and the vacuum pump 68. The control module 70 is configured to provide control signals for automating operation of the liquid impingement system 150. In some embodiments, the control module 70 includes a programmable logic circuit. In some embodiments, the control module 70 is configured to receive control instructions from an external system configured to utilize the liquid impingement system. The liquid impingement system 150 can also include a user interface (not shown) to enable a user to provide start and stop commands, refill instructions, and to provide system status to the user.

The liquid impingement system 150 automatically maintains the volume of buffer solution 60 in the collection vessel 52 within a determined range. The liquid impingement system 150 is also configured to automatically initialize the system with an initial volume of buffer solution 60. To initialize the system, the lid 58 is sealed onto the collection vessel 52, where the buffer solution has yet to be added. A start sequence is initiated and the control module 70 signals the fluid pump 64 to deliver a defined initial volume of the buffer solution from the buffer solution container 66. In some embodiments, the start sequence is initiated by a start command provided by the user or provided by an externally coupled system. After the initial volume of buffer solution is added to the collection vessel 52, an air collection system including the liquid impingement system is actuated to start delivering air through the air nozzle 54. After a set period of time, the control module 70 instructs the fluid pump 64 to pump the second volume of buffer solution into the collection vessel 52, thereby maintaining the volume of buffer solution 60 in the collection vessel 52 within the determined range.

Figure 4:
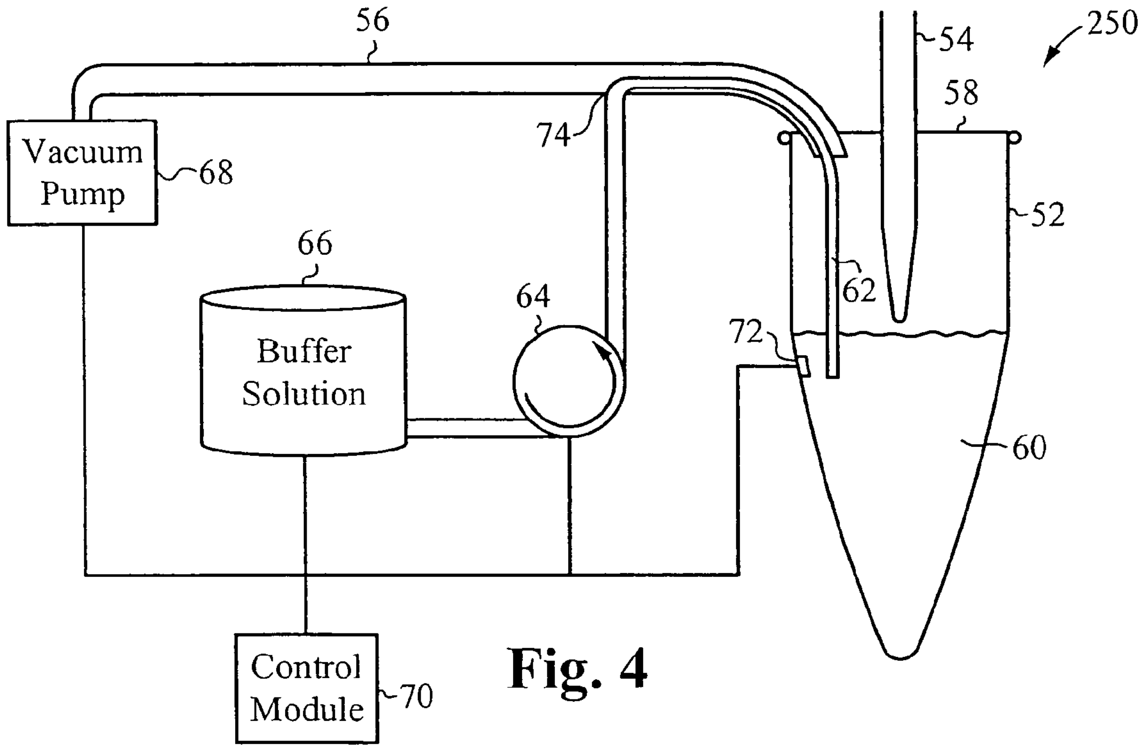
FIG. 4 illustrates an alternative embodiment of an automated version of the liquid impingement system of FIG. 2.

FIG. 4 illustrates an alternative embodiment of an automated version of the liquid impingement system of FIG. 2. The liquid impingement system 250 includes the liquid impingement system 150 of FIG. 3 and a sensor 72 coupled to the collection vessel 52. The sensor 72 is also coupled to the control module 70 via a wired or wireless connection. In some embodiments, the sensor 72 is positioned within the collection vessel 52. Alternatively, the sensor 72 is positioned external to the collection vessel 52. In this alternative embodiment, some or a portion of the collection vessel is optically transparent and the sensor includes optical detection means, such as a laser and a photo sensor array, for detecting the level of the buffer solution within the collection vessel. The sensor 72 represents a single sensor or a plurality of sensors. The sensor 72 monitors the volume of the buffer solution 60 within the collection vessel 52. When the volume of the buffer solution 60 decreases below a predetermined threshold, the control module 70 instructs the fluid pump 64 and the buffer solution container 66 to deliver the second volume of buffer solution to the collection vessel 52.

Although the embodiments of the liquid impingement units described in relation to FIGS. 2-4 are directed to a single air nozzle, a single vacuum tube, and a single fluid delivery tube, alternative embodiments are also contemplated including one or more air nozzles, one or more vacuum tubes, and/or one or more fluid delivery tubes. Similarly, alternative embodiments are also contemplated in which the liquid impingement system includes one or more fluid pumps, one or more vacuum pumps, and/or one or more control modules.

The present invention has been described in terms of specific embodiments incorporating details to facilitate the understanding of the principles of construction and operation of the invention. The specific configurations shown and the methodologies described in relation to the liquid impingement unit are for exemplary purposes only. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A liquid impingement unit comprising:

a. a collection chamber partially filled with a buffer solution;

b. an air nozzle configured to output air including airborne particles, wherein a first end of the air nozzle is positioned within the collection chamber proximate the buffer solution such that air output from the first end impinges the buffer solution, whereby the airborne particles are collected within the buffer solution;

c. a vacuum tube configured to intake air through a first end, wherein the first end of the vacuum tube is positioned within the collection chamber;

d. a fluid delivery tube configured to output additional buffer solution through a first end, wherein the fluid delivery tube is positioned within the vacuum tube such that the first end of the fluid delivery tube is positioned within the collection chamber; and e. a cover coupled to the collection chamber, the air nozzle, and the vacuum tube and configured to seal the collection chamber while providing access to the collection chamber for the air nozzle and the vacuum tube.

2. The liquid impingement system of claim 1 wherein the fluid delivery tube extends out of the first end of the vacuum tube.

3. The liquid impingement system of claim 2 wherein the first end of the fluid delivery tube is positioned proximate to the buffer solution in the collection chamber.

4. The liquid impingement system of claim 2 wherein the first end of the fluid delivery tube is positioned within the buffer solution in the collection chamber.

5. The liquid impingement system of claim 1 wherein the vacuum tube includes an aperture external to the collection vessel through which the fluid delivery tube enters the vacuum tube such that a first portion of the fluid delivery tube is positioned within the vacuum tube and a second portion of the fluid delivery tube is positioned external to the vacuum tube.

6. The liquid impingement system of claim 1 wherein the collection chamber comprises a centrifuge tube.

7. The liquid impingement system of claim 1 wherein the seal is an hermetic seal.

8. A liquid impingement system comprising:

a. a sealed collection chamber including a first volume of a buffer solution;

b. an air nozzle configured to output air including airborne particles, wherein a first end of the air nozzle is positioned within the collection chamber;

c. a vacuum tube configured to intake air through a first end, wherein the first end of the vacuum tube is positioned within the collection chamber;

d. a fluid delivery tube positioned within the vacuum tube such that a first end of the fluid delivery tube is positioned within the collection chamber;

e. a fluid pump coupled to the fluid delivery tube;

f. a buffer solution container coupled to the fluid pump, wherein the fluid pump is configured to pump buffer solution from the buffer solution container through the fluid delivery tube such that buffer solution is directed into the collection chamber; and g. a control module coupled to the fluid pump and configured to provide control signals to the fluid pump such that a second volume of buffer solution is provided into the collection chamber from the buffer solution container.

9. The liquid impingement system of claim 8 wherein the first end of the air nozzle is positioned proximate to the buffer solution such that air output from the first end impinges the buffer solution, whereby the airborne particles are collected within the buffer solution.

10. The liquid impingement system of claim 9 wherein the second volume and the period are determined by an evaporation rate of the buffer solution within the collection chamber.

11. The liquid impingement system of claim 10 wherein the control module is configured to provide control signals to the fluid pump such that the second volume of buffer solution is directed into the collection chamber on a periodic basis.

12. The liquid impingement system of claim 8 further comprising a sensor positioned within the collection chamber and configured to detect a minimum threshold level of the buffer solution within the collection chamber.

13. The liquid impingement system of claim 12 wherein the control module is configured to receive a minimum threshold level signal from the sensor and in response to minimum threshold level signal the control module is configured to provide control signals to the fluid pump such that the second volume of buffer solution is directed into the collection chamber.

14. The liquid impingement system of claim 8 wherein the control module is configured to initialize the system by providing control signals to the pump to provide the first volume of buffer solution into the collection chamber.

15. The liquid impingement system of claim 8 wherein the collection chamber comprises a centrifuge tube.

16. The liquid impingement system of claim 8 wherein the seal is an hermetic seal.

17. The liquid impingement system of claim 8 further comprising an air intake system coupled to the air nozzle.

18. The liquid impingement system of claim 8 wherein the vacuum tube includes an aperture external to the collection vessel through which the fluid delivery tube enters the vacuum tube such that a first portion of the fluid delivery tube is positioned within the vacuum tube and a second portion of the fluid delivery tube is positioned external to the vacuum tube.

19. The liquid impingement system of claim 18 further comprising a vacuum pump coupled to a second end of the vacuum tube.

20. A liquid impingement system comprising:

a. a liquid impingement unit comprising:

i. a sealed collection chamber including a first volume of a buffer solution;

ii. an air nozzle configured to output air including airborne particles, wherein a first end of the air nozzle is positioned within the collection chamber; and iii. a vacuum tube configured to intake air through a first end, wherein the first end of the vacuum tube is positioned within the collection chamber;

b. a fluid delivery tube including a first portion which is entirely positioned within the vacuum tube such that a first end of the fluid delivery tube is positioned within the collection chamber, and a second portion which exits the vacuum tube through a vacuum tube aperture;

c. a vacuum pump coupled to a second end of the vacuum tube;

d. a fluid pump coupled to a second end of the fluid delivery tube;

e. a buffer solution container coupled to the fluid pump, wherein the fluid pump is configured to pump buffer solution from the buffer solution container through the fluid delivery tube such that buffer solution is directed into the collection chamber; and f. a control module coupled to the fluid pump and configured to provide control signals to the fluid pump such that a second volume of buffer solution is provided into the collection chamber from the buffer solution container.

* * * * *

UNITED STATES PATENT AND TRADEMARK OFFICE

CERTIFICATE OF CORRECTION

PATENT NO. : 7,699,915 B2
APPLICATION NO. : 11/509879
DATED : April 20, 2010
INVENTOR(S) : Chun-Wah (Phil) Lin It is certified that error appears in the above-identified patent and that said Letters Patent is hereby corrected as shown below:

IN THE CLAIMS

At column 6, line 52, Claim 10, please change the dependency of Claim 10 from Claim 9 to Claim 11.

At column 6, line 55, Claim 11, please change the dependency of Claim 11 from Claim 10 to Claim 8.

Signed and Sealed this

First Day of June, 2010

David J. Kappos

*Director of the United States Patent and Trademark Office*